United States Patent
Döpper et al.

(10) Patent No.: US 6,482,189 B2
(45) Date of Patent: *Nov. 19, 2002

(54) PATIENT CONNECTOR FOR PERITONEAL DIALYSIS

(75) Inventors: Joachim Döpper, Gross-Gerau (DE); Wolfgang Schulz, St. Wendel (DE)

(73) Assignee: Fresenius Medical Care Deutschland GmbH, Bad Homburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/280,027

(22) Filed: Mar. 26, 1999

(65) Prior Publication Data

US 2001/0041873 A1 Nov. 15, 2001

(30) Foreign Application Priority Data

Mar. 30, 1998 (GB) .......................... 19814047

(51) Int. Cl.[7] ............................... A61M 25/00
(52) U.S. Cl. ..................................... 604/284
(58) Field of Search ................. 604/533, 523, 604/539, 284, 246, 256, 29, 30, 31, 33, 34, 236, 213, 318, 319, 324, 325, 167.01, 167.02, 167.03, 167.04, 167.05, 249, 247, 237, 238

(56) References Cited

U.S. PATENT DOCUMENTS

| 3,081,770 | A | * | 3/1963 | Hunter | 128/221 |
| 4,655,762 | A | * | 4/1987 | Rogers | 604/403 |
| 5,743,872 | A | * | 4/1998 | Kelly | 604/49 |
| 5,766,151 | A | * | 6/1998 | Valley et al. | 604/96 |
| 5,785,693 | A | * | 7/1998 | Haining | 604/249 |

FOREIGN PATENT DOCUMENTS

DE    44 43 714 C2    6/1996

* cited by examiner

Primary Examiner—Anhtuan T. Nguyen
Assistant Examiner—Ann Y Lam
(74) Attorney, Agent, or Firm—Henry M. Feiereisen

(57) ABSTRACT

A connector for use in peritoneal dialysis, includes a base body having a first tube for attachment of a container for dialysis solution, and a second tube for attachment of a peritoneal catheter. Positioned in a passageway between the first tube and the second tube is a closure piece which so interacts with an actuator that an operation of the actuator causes the closure piece to move in a linear direction from a first position into a second position in which the fluid flow between the first tube and the second tube is closed while the first tube is sealed off.

8 Claims, 1 Drawing Sheet

PATIENT CONNECTOR FOR PERITONEAL DIALYSIS

CROSS-REFERENCES TO RELATED APPLICATIONS

This application claims the priority of German Patent Application Serial No. 198 14 047.9-44, filed Mar. 30, 1998, the subject matter of which is incorporated herein by reference.

BACKGROUND OF THE INVENTION

The present invention relates, in general, to a patient connector for peritoneal dialysis, and more particularly to a connector of a type including a base body having a first tube for attachment of a container for dialysis solution, and a second tube for attachment to a peritoneal catheter.

Peritoneal dialysis is a type of dialysis therapy that utilizes the membrane in a patient's peritoneal cavity for the purpose of separating waste products from the patient's fluid system. One type of peritoneal dialysis is referred to as continuous ambulatory peritoneal dialysis (CAPD) in which a dialysis solution is introduced from a solution bag into the patient's peritoneal cavity by a peritoneal catheter, with the dialysis solution exhibiting a concentration gradient in relation to body-own fluids. Toxic substances enter the peritoneal cavity via the peritoneum that acts as the membrane. After a few hours, spent fluid is drained from the peritoneal cavity to a drain bag, and fresh fluid is infused from another solution bag. To regulate the fluid flow through the tubing set, a connector is secured to the abdomen-side section of the peritoneal catheter and communicates with a bag containing fresh dialysis solution and with a bag receiving spent dialysis solution.

German Pat. No. 44 43714 C2 discloses a patient connector of the above type which includes a housing arranged between the tubes for fresh and spent dialysis solutions and the peritoneal catheter. Positioned in the housing are closure pieces which can be so actuated as to realize the individual steps to exchange the dialysis fluid in the abdominal cavity of the patient, whereby the closure pieces execute a displacement in radial direction upon operation of a rotary mechanism which rotates only in one direction. This apparatus has a very complicated structure.

SUMMARY OF THE INVENTION

It is thus an object of the present invention to provide an improved patient connector, obviating the afore-stated drawbacks.

In particular, it is an object of the present invention to provide an improved patient connector for peritoneal dialysis, which is simple in structure.

These objects, and others which will become apparent hereinafter, are attained in accordance with the present invention by providing a base body having a first tube for attachment of a container for dialysis solution, and a second tube for attachment to a peritoneal catheter, a closure piece accommodated in the base body and so disposed in a first position between the first tube and the second tube as to allow a fluid flow between the first tube and the second tube, and an actuator provided on the base body and so interacting with the closure piece that an operation of the actuator causes the closure piece to move in a linear direction from the first position into second position in which the fluid flow between the first tube and the second tube is closed while the first tube is sealed off.

The invention is based on the recognition that a peritoneal dialysis can be carried out while the patient is asleep by using valves, i.e. closure pieces, to control the inflow and drain of solution into and from the peritoneum. As the valves in this case clear and close the tubes, the use of a three-way valve, as disclosed in German Pat. No. 44 43 714 C2, is no longer required as only one passageway leads to the peritoneal catheter. Once, the peritoneal dialysis is concluded, the patient is released from the patient connector according to the present invention in a simple, safe and rapid manner.

According to another feature of the present invention, the actuator may be positioned in coaxial relationship with the second tube. In the event the actuator is operated by the patient, an internal pin closes the connector to the patient, and the advancing closure piece seals off the inflow and drain simultaneously with a sealing of the peritoneal catheter.

The first tube terminates in a port which is suitably positioned laterally in the base body between the actuator and the closure piece, whereby the base body may extend essentially linear.

According to yet another feature of the present invention, the actuator may include a sealing element which is shiftable in linear movement to a location in front of the port of the first tube in the second position. The actuator may be connected to the sealing element, or may be separate from the sealing element.

Preferably, the movement of the closure piece from the first position into the second position is irreversible.

According to still another feature of the present invention, the closure piece is retained by a cage in the first position.

The sealing element is preferably of substantially cylindrical configuration and has two sealing lips, respectively disposed on the forward and rearward ends of the sealing element.

Advantageously, the sealing element has a length which is greater than a diameter of the port of the first tube.

The advantages of the connector according to the present invention reside primarily in the simpler structure and easy handling, compared to conventional patient connectors. Thus, the connector according to the present invention provides an optimum solution for valve-controlled peritoneal dialysis while the patient is asleep.

BRIEF DESCRIPTION OF THE DRAWING

The above and other objects, features and advantages of the present invention will now be described in more detail with reference to the accompanying drawing, in which.

DETAILED DESCRIPTION OF PREFERRED EMBODIMENTS

Figure 1:
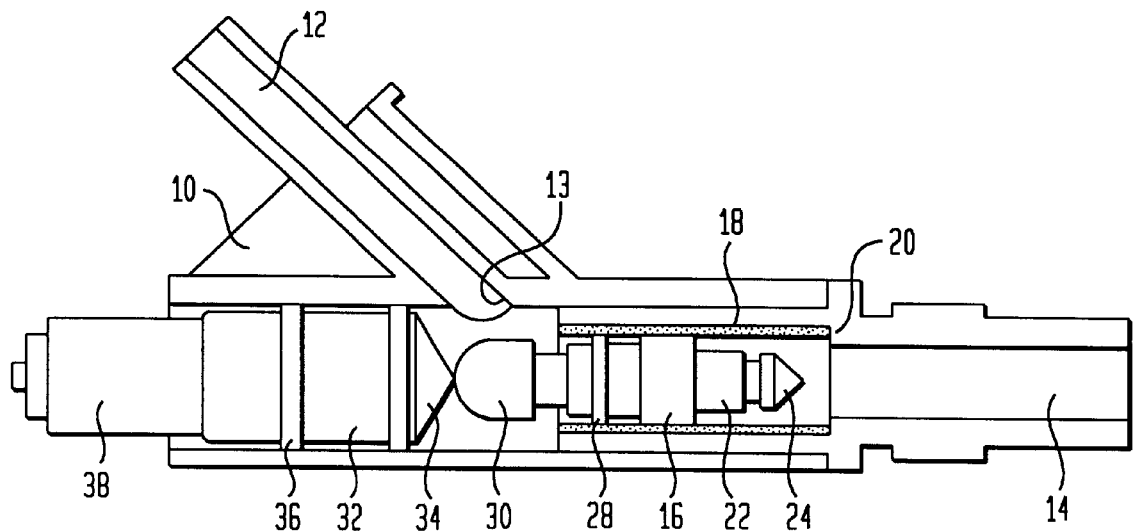
FIG. 1 is a side elevational view of a patient connector according to the present invention in first position.

Throughout all the Figures, same or corresponding elements are generally indicated by same reference numerals.

Turning now to the drawing, and in particular to FIG. 1, there is shown a side elevational view of a patient connector according to the present invention, including a substantially linear base body 10 which has a tube 12 for attachment of a bag (not shown) with dialysis solution and a tube 14 which projects out from the main body 10 in coaxial relationship for attachment to a peritoneal catheter (not shown). Accommodated in the base body 10 is a closure piece 16 which extends coaxially to the second tube 14 and is retained in a cage 18. At the junction to the main body 10, the tube 14 is formed with a shoulder 20 upon which one axial end of the cage 18 is seated. FIG. 1 shows the closure piece 16 in its idle first position in which dialysis solution can flow from the bag through the tube 12 and the main body 10 into the tube 14 and ultimately into the peritoneal catheter.

The closure piece 16 is formed in fluid flow direction with a forward entry member 22 which has a conical tip 24 to facilitate insertion into the tube 14. Connected to the entry member distal end face of the closure piece 16 is a rearward member 26 which is formed with a sealing lip 28 and terminates in a rear bulbed end 30. Trailing the closure piece 16 is a sealing element 32 which is of substantially cylindrical configuration, with a forward conical tip 34 which rests against the bulbed end 30 of the closure piece 16. Immediately adjacent the forward conical tip 34 and at the rear end thereof, the sealing element 32 has two sealing lips 36.

As shown in FIG. 1, the tube 12 extends obliquely with respect to the base body 10 and has a port 13 which enters the base body 10 laterally between the sealing element 32 and the closure piece 16, whereby the tube 14, the closure piece 16 and the sealing element 32 are arranged axially behind one another. The length of the sealing element 32 exceeds the diameter of the lateral port 13 of the tube 12 so that the sealing element 32 is capable of closing the port 13. In the idle position, shown in FIG. 1, the sealing element 32 seals the rear area of the substantially cylindrical base body 10.

In the nonlimiting example of FIG. 1, the sealing element 32 is formed integrally on an actuator 38 which serves as push button and closes the rear end of the base body 10. Persons skilled in the art will understand that the actuator may also form a component that is separate from the sealing element and can be advanced into the interior of the base body against the sealing element via a screwed connection.

Figure 2:
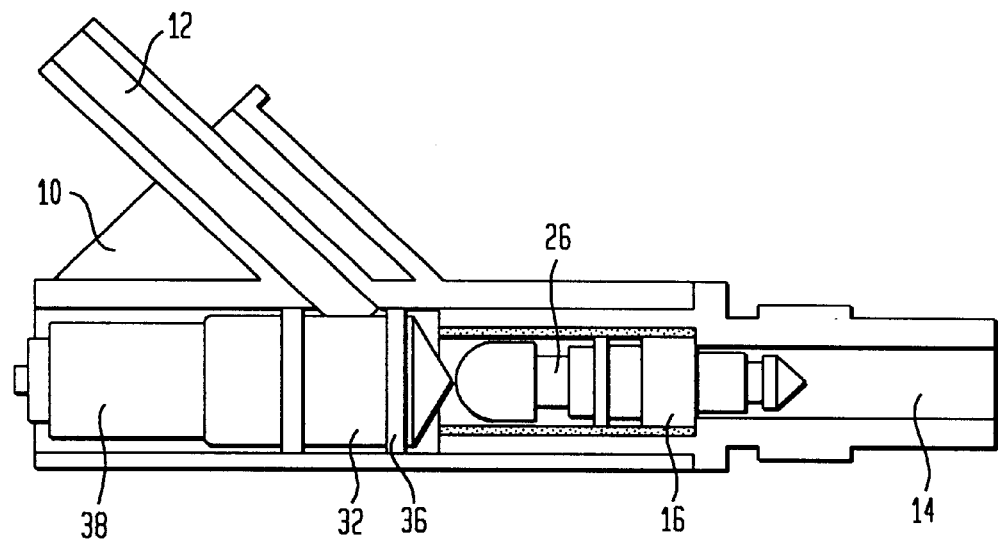
FIG. 2 is a side elevational view of the patient connector of FIG. 1 in second position.

Displacement of the actuator 38 results in a linear movement of the sealing element 32 and the closure piece 16 into a second operative position, as shown in FIG. 2, in which the closure piece 16 travels out of the cage 18, with the forward member 22 entering the tube 14 until the closure piece 16 rests against the shoulder 20. The tube 14 is then closed off. At the same time, the sealing element 32 is pushed into a position in front of the port 13 of the tube 12 so that the port 13 is positioned between the sealing lips 36 and thereby sealed off. Thus, also the rear area of the base body 10 is sealed.

The operation of the actuator 38 is irreversible, i.e. the forward motion of the actuator 38 cannot be reversed, and thus the actuator 38 cannot be operated again after actuated once so that the initiated linear displacement of the sealing element 32 and the closure piece 16 is final.

While the invention has been illustrated and described as embodied in a patient connector for peritoneal dialysis, it is not intended to be limited to the details shown since various modifications and structural changes may be made without departing in any way from the spirit of the present invention.

What is claimed as new and desired to be protected by Letters Patent is set forth in the appended claims:

What is claimed is:

1. A connector for use in peritoneal dialysis, said connector comprising:

a base body having a first tube configured for attachment of a container for dialysis solution, and a second tube configured for attachment of a peritoneal catheter;

a closure piece accommodated in the base body and so disposed in a first position between the first tube and the second tube as to allow a fluid flow between the first tube and the second tube;

an actuator positioned coaxial with the second tube and slidingly received in the base body, wherein the first tube terminates in a port positioned laterally in the base body between the actuator and the closure piece: and a sealing element positioned between the actuator and the closure piece and disconnected from the closure piece, wherein the actuator is configured to interact with the closure piece such that an operation of the actuator irreversibly moves the closure piece via the sealing element in a linear direction from the first position into a second position in which the closure piece rests against a shoulder of the base body to cut the fluid flow between the first tube and the second tube while the sealing element seals off the first tube.

2. The connector of claim 1 wherein the base body extends essentially linear.

3. The connector of claim 1 wherein the sealing element is shiftable in linear movement in front of the port of the first tube upon actuation of the actuator, when the closure piece occupies the second position.

4. The connector of claim 1 wherein the actuator is connected to the sealing element.

5. The connector of claim 1 wherein the actuator and the sealing element are separate components.

6. The connector of claim 1, and further comprising a cage for retaining the closure piece in the first position.

7. The connector of claim 1 wherein the sealing element is substantially of cylindrical configuration and has opposite ends, said sealing element having two sealing lips, one sealing lip positioned on one of the ends of the sealing element and another sealing lip positioned on the other one of the end of the sealing element.

8. The connector of claim 1 wherein the sealing element has a length which is greater than a diameter of the port of the first tube.

\* \* \* \* \*

UNITED STATES PATENT AND TRADEMARK OFFICE
CERTIFICATE OF CORRECTION

PATENT NO. : 6,482,189 B2
DATED : November 19, 2002
INVENTOR(S) : Joachim Döpper and Wolfgang Schulz It is certified that error appears in the above-identified patent and that said Letters Patent is hereby corrected as shown below:

<u>Title page,</u>
Item [30], Foreign Application Priority Data,
Replace "March 30, 1998 (GB) ...............19814047" with
-- March 30, 1998 (DE) ................19814047 --

Signed and Sealed this

Fifth Day of August, 2003

JAMES E. ROGAN
*Director of the United States Patent and Trademark Office*